(12) United States Patent
Fricke et al.

(10) Patent No.: US 7,732,354 B2
(45) Date of Patent: *Jun. 8, 2010

(54) FLAT IMPLANT OF TEXTILE THREAD MATERIAL, IN PARTICULAR HERNIA MESH IMPLANT

(75) Inventors: Helmut Fricke, Meinersen-Ahnsen (DE); Johannes Buttstädt, Cadolzburg (DE)

(73) Assignee: GfE Medizintechnik GmbH (DE)

( * ) Notice: Subject to any disclaimer, the term of this patent is extended or adjusted under 35 U.S.C. 154(b) by 1556 days.

This patent is subject to a terminal disclaimer.

(21) Appl. No.: 10/513,316

(22) PCT Filed: May 6, 2003

(86) PCT No.: PCT/EP03/04732

§ 371 (c)(1),
(2), (4) Date: Nov. 3, 2004

(87) PCT Pub. No.: WO03/094781

PCT Pub. Date: Nov. 20, 2003

(65) Prior Publication Data

US 2005/0228408 A1    Oct. 13, 2005

(30) Foreign Application Priority Data

May 7, 2002    (DE)    ................... 102 21 320

(51) Int. Cl.
  B32B 27/12    (2006.01)
  B32B 27/04    (2006.01)
  D03D 9/00    (2006.01)
  A61B 17/08    (2006.01)
(52) U.S. Cl. .................. 442/2; 442/6; 442/43; 442/46; 442/49; 606/151
(58) Field of Classification Search ................. 606/151; 442/2, 6, 43, 46, 49
See application file for complete search history.

(56) References Cited

U.S. PATENT DOCUMENTS

| 4,839,215 A | 6/1989 | Starling et al. |
| 5,292,328 A * | 3/1994 | Hain et al. .................. 606/151 |
| 2004/0172048 A1 * | 9/2004 | Browning .................. 606/151 |

FOREIGN PATENT DOCUMENTS

| DE | 19832634 | * | 9/1998 |
| EP | 1 099 421 A | | 5/2001 |
| WO | WO 0222047 | | 3/2002 |

* cited by examiner

Primary Examiner—Ula C Ruddock
(74) Attorney, Agent, or Firm—DeMont & Breyer, LLC

(57) ABSTRACT

The invention relates to a flat implant of textile thread material, in particular a hernia mesh implant, in the form of single-layered mesh fabric (1) of a basis weight of 5 to 40 g/m².

17 Claims, 3 Drawing Sheets

FLAT IMPLANT OF TEXTILE THREAD MATERIAL, IN PARTICULAR HERNIA MESH IMPLANT

Figure 1:
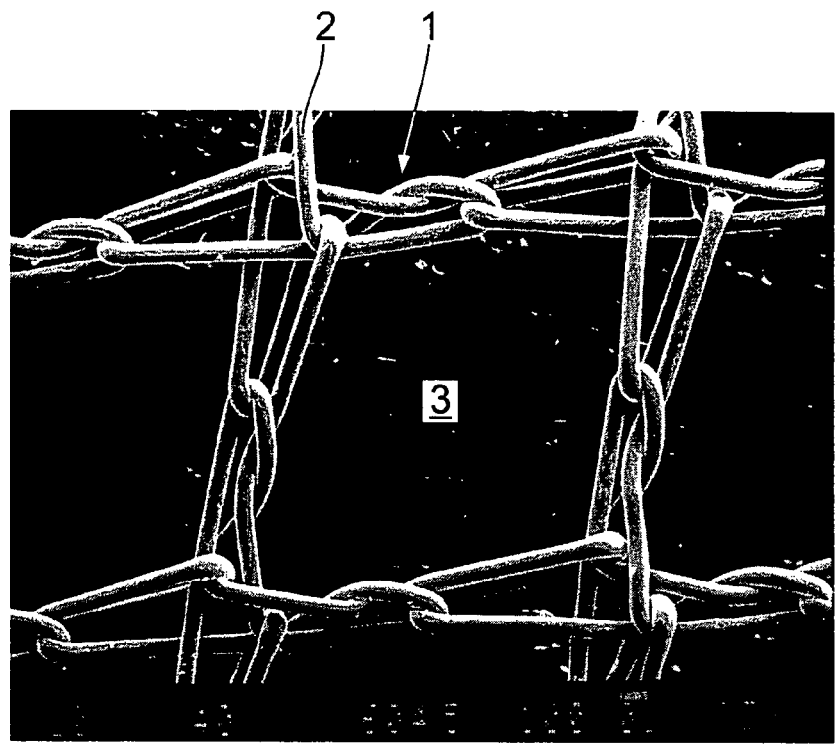

The invention relates to a flat implant of textile thread material, in particular a hernia mesh implant. Approximately three percent of a country's inhabitants are affected by inguinal hernia in the course of their lives. Hernia surgery belongs to the most frequent surgical procedures worldwide. More than 75 percent of those patients are treated with surgical techniques that involve closing the abdominal gap with plastic mesh fabric, a so-called hernia mesh implant.

For successful, long-term hernia repair based on the use of plastic mesh fabric, the implant must comply with the following requirements:
chemically inert
no physical changes in contact with body fluids
not triggering inflammatory response and foreign-body reaction
not cancerogenic
anallergenic
resistant to mechanical strain
sterilizable and
produceable in the shape needed.

Today's surgery makes use primarily of the below-listed, three plastic materials as hernia-mesh base material:
polyester (PET)
polytetrafluoroethylene (PTFE) and
polypropylene (PP).

Furthermore, the design of the mesh fabric varies in the kind of weaving and knitting. Monofilament and multifilament mesh fabrics are conceivable just as well as non-wovens, which vary in the size of meshes and loops and in basis weight. A major part of hernia operations based on the use of plastic mesh fabric have clinically satisfying results. Recurrences amount to less than ten percent. However, complications caused by plastic mesh implantation are reported over and over again. There is a need for mesh fabric of optimal tolerance by a patient. Decisive demands on newly developed mesh fabrics reside in inflammatory responses being reduced to a minimum and tolerance of the mesh fabric by the human body being raised to a maximum.

The object of the invention resides in that the flat implant of textile thread material, in particular the hernia mesh implant, is provided in the form of single-layered mesh fabric of a basis weight of 5 to 40 $g/m^2$.

Strong reduction of the basis weight of the mesh fabric or implant offers numerous advantages in implant handling and take. To begin with, the quantity of implanted foreign body is reduced, this reducing any irritation of the connective tissue and rejection. Furthermore, the low quantity of material renders the implant extraordinarily flexible so that it snugly fits body surfaces, staying in the position once taken.

By advantage, the mesh fabric includes surface metallization, preferably containing titanium. Metallizations of this kind, which are based on the use of PACVD processes, have been known for example from DE 199 45 299 A. Surface metallization of the threads in particular with titanium offers excellent tissue tolerance.

The basis weight of the mesh fabric according to the invention advantageously ranges from 10 to 39 $g/m^2$, preferably to 37 $g/m^2$. Preferably the threads are monofilaments. Various designs of mesh fabric are available. In an especially preferred embodiment of the invention the mesh fabric is made from individually supplied monofilaments. In these designs, the basis weight preferably ranges from 10 to 20 $g/m^2$, in particular 16 $g/m^2$ or, in case of more strongly designed monofilaments, it amounts to 32 to 39 $g/m^2$. In keeping with another embodiment of the invention, the mesh fabric is made from doubly supplied monofilaments. In this case the basis weight ranges in particular from 20 to 37 $g/m^2$, as a rule approximately 35 to 37 $g/m^2$.

Thread thickness is low too. Preferably it is in the range of 10 to 150 µm, in particular between 30 and 80 µm. Thread gauges in the range of 70 to 75 µm, in particular 60 to 70 µm, have proved to be of special advantage. The fineness ranges from approximately 8 to 70 dtex, in particular approximately 30 dtex. However, successfully used implants may just as well have thread gauges of 90 µm (corresponding to 58 dtex).

By advantage the mesh fabric is hosiery or knit fabric, there being a preference for hosiery, in particular warp-knit hosiery. Open-worked hosiery structures, or structures that are not open, have made an excellent account of themselves, in particular transparent structures. One-guide-bar or two-guide-bar warp knitting machines have qualified for the manufacture. Preferred textures are as follows: warp satin, silk net and open work. Mesh density may vary within wide ranges, advantageously being in the range of 2,500 to 25,000, in particular 4,000 to 14,000 meshes per square decimeter, more preferably 12,000 meshes per square decimeter. In practice, mesh densities ranging between 5,000 and 11,000, in particular 5,000 and 7,000, have proved to be favorable. Mesh fineness is advantageously in the range of E8 to E44 (needles per inch).

The mesh fabric according to the invention is highly porous, its porosity advantageously being in the range of 65 to 85 percent, in particular in the range of 70 to 80 percent. A porosity of approximately 73 to 75 percent has made a good account of itself in practice. Advantageously the mesh fabric is transparent, which has proved efficient when it is placed during surgery. The mesh fabric has comparatively great, clear mesh apertures in the size of 0.3 to 2 $mm^2$, in particular 0.5 to 1.5 $mm^2$. Clear mesh apertures of approximately 1 $mm^2$ have proved successful. Latticed mesh fabric has proved rather efficient. Especially preferred embodiments have mesh apertures in the form of squares or parallelograms enclosed by thin lattice ribs. By advantage, the mesh texture is warp satin. The threads in the vicinity of the lattice ribs have loops, with a rib thickness of three threads resulting in the case of monofilament threads. If two parallel monofil threads are used, a thickness of six threads results for each rib, as can be seen from the ensuing description of exemplary embodiments.

Non resorbable, inert plastic material is an especially suitable material for the implants according to the invention, polypropylene being preferred. By advantage the implant according to the invention consists exclusively of non resorbable material. Apart from being metallized, it does not have any impregnation or coating.

The thickness of the mesh fabric or implant according to the invention is preferably in the range of 0.10 to 0.40 mm, in particular 0.15 to 0.30 mm, a thickness of approximately 0.20 mm being of special advantage.

Tests have shown that, using laparoscopic surgical technique, the mesh fabric according to the invention can easily be placed on the inside of the abdominal wall, where it adheres by its low weight. This is still supported by the fact that the surface metallization, which contains in particular a titanium alloy, provides for hydrophilizing the mesh fabric. As a result of the improved wettability, the hernia mesh implant sticks to the tissue that is to be supported, sucking at it as it were, which provides for the mesh implant that has been inserted by laparascopy to unfurl more readily. As a result, there is no risk of a mesh implant slipping or plying when a cavity that has been prepared by laparoscopy is closed again. On the whole, placing the mesh implant is more easily feasible than with comparable, heavier mesh structures. The low amount of material that is inserted when the mesh implant according to the invention is placed, and in particular its thin, lightweight, wide-meshed and flexible structure give excellent long-term results.

Figure 2:
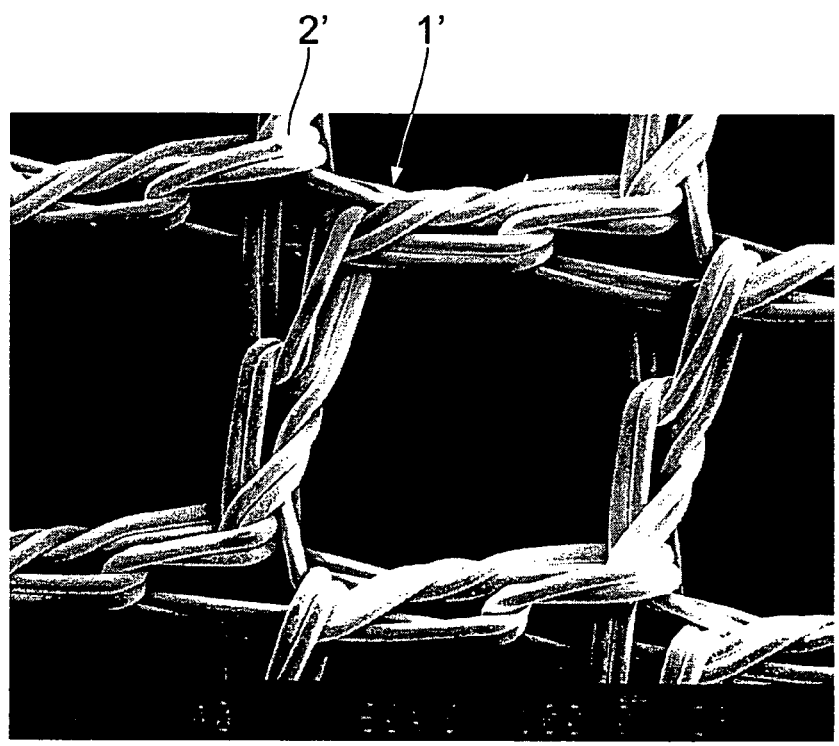
Figure 3:
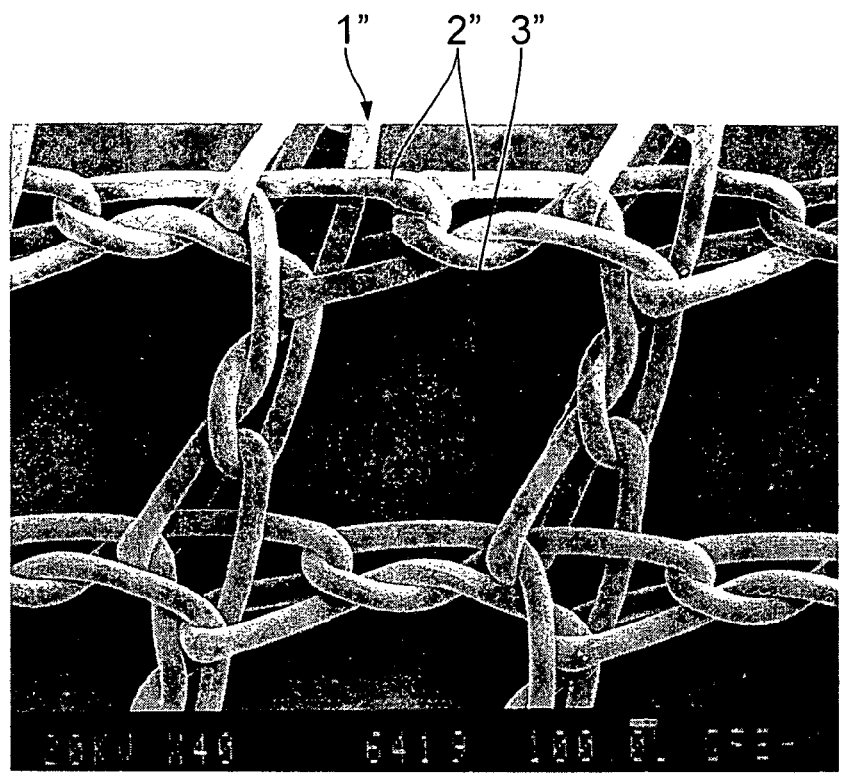
Figure 4:
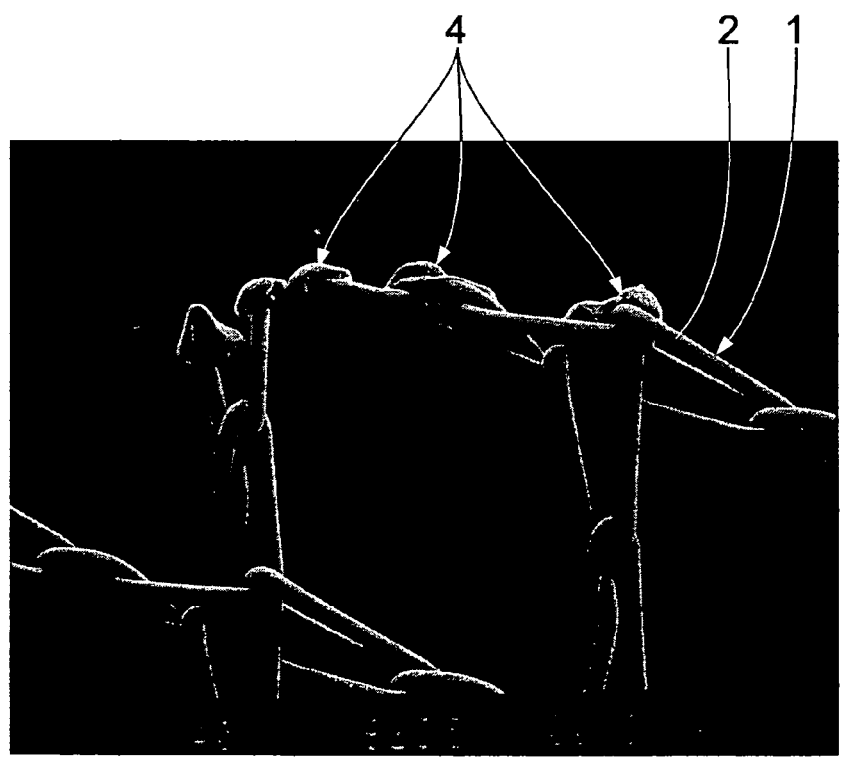
Figure 5:
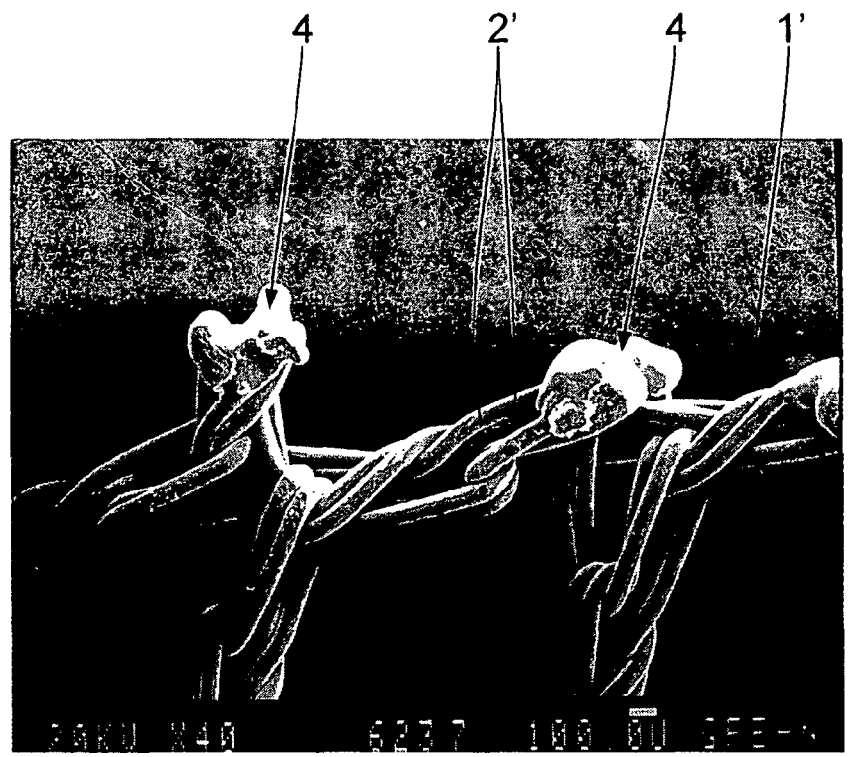
Figure 6:
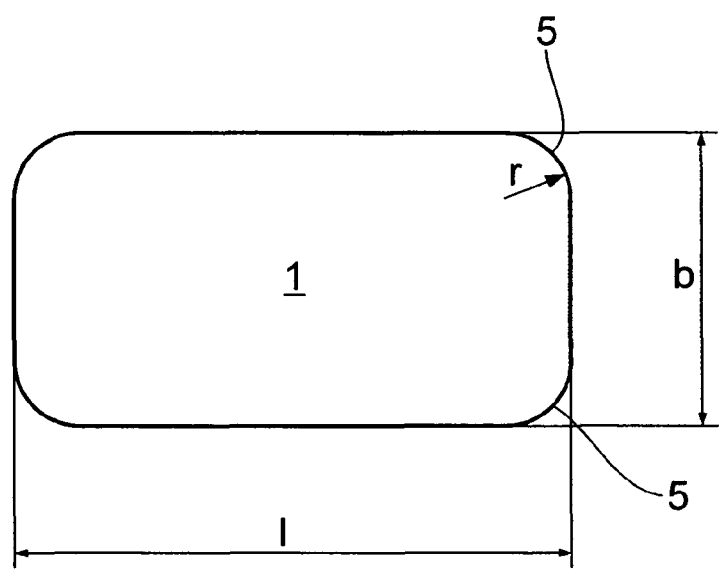

Further features, details and advantages of the invention will become apparent from the ensuing description of exemplary embodiments of lightweight hernia mesh fabrics, taken in conjunction with the drawings, in which FIGS. 1 to 3 are enlarged views of details of three different embodiments of lightweight hernia mesh fabrics;

FIGS. 4 and 5 are enlarged views of details of the hernia mesh fabrics according to FIGS. 1 and 2 in the vicinity of the edge of cut thereof; and FIG. 6 is an outline drawing of a hernia mesh implant.

The embodiment of the invention seen in FIG. 1 of the drawing illustrates details of hernia mesh fabric 1 enlarged forty times. Monofil polypropylene threads 2 of a thickness of 66 μm have been worked into two-rowed warp satin on a warp knitting machine, forming coarse meshes. This kind of knitting has produced a lattice structure with apertures 3 of the type of a parallelogram, the acute angle of the parallelogram being in the range of approximately 80°. The size of the apertures 3 amounts to approximately 1 mm. The individual threads 2 of the lattice structure are deviated, forming loops, so that the lattice ribs, at any spot, are comprised of a triplicate of individual threads 2. The mesh fabric 1 comprises approximately 10,800 meshes per square decimeter. The basis weight of the mesh fabric amounts to 16 g/m$^2$. The resistance to tear of the mesh fabric clearly exceeds the resistance to tear of the tissue that is to be supported (approximately 16 N/cm). Along the lines of DIN 53857, maximum tensile force is $\geq$50 N in length and $\geq$40 N in width. Maximum tensile strain is in the range of $\geq$20% in length and $\geq$40% in width.

The edges of the mesh fabric 1, which has been cut to a desired size of approximately 10×10 cm to 30×30 cm, can be skeined thermally or by glue. The porosity of the mesh fabric is in the range of 80%. It is excellently transparent. The mesh fabric has a single-layer design. It has a thickness of approximately 0.20 mm and is very flexible. In a surgical operation the mesh fabric can easily be placed on the inside of a patient's abdominal wall where it adheres by itself. The surface of the mesh fabric is metallized by plasma deposition (PACVD), having a titanium film so thin that the metal is not perceptible to the naked eye. Due to the low amount of material, the inferior surface of the plastic threads and histocompatibility by metallization of the polypropylene surface, the mesh fabric offers excellent take and permanently good results.

The mesh fabric 1' of the embodiment seen in FIG. 2 is made from the same thread material, possessing the same texture as the embodiment of FIG. 1. The mesh fabric is also metallized with titanium. But, as compared to FIG. 1, two monofil threads are supplied in parallel as a double thread 2'. As a result, the mesh fabric 1' has approximately twice the basis weight of 37 g/m$^2$. The lattice structure is substantially square. Again the texture is warp satin. With two monofil threads being supplied in parallel, the number of threads is six at any spot of the lattice structure. In spite of twice the number of threads, the clear mesh aperture of the mesh fabric 1' is approximately the same as in the embodiment of FIG. 1. The number of meshes is approximately 10,000 meshes per square decimeter. Porosity of the mesh fabric is in the range of 73%. The thickness of the mesh fabric is 0.25 mm. Along the lines of DIN 53857, the maximum tensile force amounts to $\geq$200 N in length and $\geq$100 N in width. The maximum tensile strain is in the range of $\geq$30% in length and $\geq$60% in width.

The mesh fabric 1" of the embodiment seen in FIG. 3 has the same texture as the embodiment of FIG. 1, also having single filament supply. However, use is made of a thicker thread 2" of a gauge of 0.090 mm (58 dtex) so that mesh fabric is created, the properties and mesh structure of which are comparable to the heavy hernia mesh fabric of FIG. 2. In this regard, the basis weight of the mesh fabric 1" amounts to 32 to 39 g/m$^2$, its thickness to 0.3 mm. In the warp satin texture used, the number of meshes is in the range of 8,300 to 13,300 meshes per square decimeter. The maximum tensile force and maximum tensile strain of the mesh fabric 1" of FIG. 3 correspond to those of the mesh fabric 1' seen in FIG. 2. The optical porosity by reason of the openings 3" is in the range of 70 percent.

The mesh fabrics of FIGS. 2 and 3 are heavier than the mesh fabric of FIG. 1, but they are sill sufficiently lightweight to possess excellent take behaviour. The mesh fabric unfurls easily upon surgery, adhering to the inside of the abdominal wall without any subsequent displacing or creasing. Long-term tests on animals have given excellent results.

Other problems of hernia mesh implants are posed by the fact that they must be cut from a wider, continuous hosiery sheet. Conventional punching processes will produce free ends of thread that might unravel.

For this to be avoided, the mesh implant pattern is laser-cut. In the process, the ends 4 of the individual threads 2, 2' fuse—as seen in FIGS. 4 and 5—which precludes any unravelling of free ends of thread. Laser-cutting thus increases the mesh implant quality.

As further seen in FIG. 6, the implant pattern of hernia mesh fabric 1 is designed for round corners 5. The radius of curvature r is in a range of 4 to 40 mm; preferably r is equal to 22 mm. The rounded corners help preclude any irritation of the body tissue after mesh fabric implantation, which would be produced mechanically by acute corners.

The outlines of the implant of hernia mesh fabric 1 amount to approximately 15 cm of length l and approximately 10 cm of width b.

The invention claimed is:

1. A flat implant of textile thread material in the form of single-layered mesh fabric (1; 1'; 1") of a basis weight of 5 to 40 g/m$^2$, wherein the mesh fabric (1; 1', 1") includes surface metallization containing titanium in the form of a thin film that is applied by plasma deposition.

2. An implant according to claim 1, wherein its basis weight amounts to 10 to 39 g/m$^2$.

3. An implant according to claim 1, wherein the mesh fabric (1, 1") is made from single-thread monofilament (2; 2") and wherein the basis weight amounts to 10 to 20 g/m$^2$ or 32 to 39 g/m$^2$.

4. An implant according to claim 1, wherein the mesh fabric (1') is made from double-thread monofilament (2') and wherein the basis weight amounts to 20 to 37 g/m$^2$.

5. An implant according to claim 1, wherein the threads (2; 2', 2") have a gauge of 10 to 150 μm.

6. An implant according to claim 1, wherein the mesh fabric (1; 1'; 1") is one of hosiery or knit fabric.

7. An implant according to claim 1, wherein the mesh fabric (1; 1') has a mesh density of 2,500 to 25,000 meshes per square decimeter.

8. An implant according to claim 1, wherein the mesh fabric (1; 1'; 1") has a porosity of 65 to 85%.

9. An implant according to claim 1, wherein the mesh fabric (1; 1'; 1") is transparent.

10. An implant according to claim 1, wherein the mesh fabric has a lattice structure comprising apertures (3; 3', 3") which are of the type of squares or parallelograms.

11. An implant according to claim 1, wherein the mesh fabric includes clear mesh apertures (3; 3'; 3") of a size of 0.3 to 2 mm$^2$.

12. An implant according to claim 1, wherein the mesh fabric (1; 1'; 1") has a warp satin texture.

13. An implant according to claim 1, wherein the mesh fabric (1; 1'; 1") entirely consists of polypropylene.

14. An implant according to claim 1, wherein the mesh fabric (1; 1'; 1") is comprised of monofil threads.

15. An implant according to claim 1, wherein the mesh fabric (1; 1'; 1") has a thickness of 0.10 to 0.40 mm.

16. An implant according to claim 1, wherein the single-layered mesh fabric (1; 1'; 1") has a rectangular basic shape with rounded corners (5), the radius of curvature (r) of which ranges between 4 and 40 mm.

17. An implant according to claim 1, wherein the edges (4) of the single-layered mesh fabric (1; 1') are laser-cut.

* * * * *

UNITED STATES PATENT AND TRADEMARK OFFICE
CERTIFICATE OF CORRECTION

PATENT NO. : 7,732,354 B2  Page 1 of 1
APPLICATION NO. : 10/513316
DATED : June 8, 2010
INVENTOR(S) : Fricke et al.

It is certified that error appears in the above-identified patent and that said Letters Patent is hereby corrected as shown below:

Title Page, Item (75) Inventors: should read Helmut Fricke, Meinersen-Ahnsen (DE), Johannes Buttstädt, Roßtal (DE)

Signed and Sealed this

Seventeenth Day of August, 2010

David J. Kappos
*Director of the United States Patent and Trademark Office*